United States Patent [19]

Pohl et al.

[11] Patent Number: 5,454,810
[45] Date of Patent: Oct. 3, 1995

[54] EXTERNAL FIXATION DEVICE

[76] Inventors: Anthony P. Pohl, 31 Myrtle Street, Seacliff, 5049; Bruce H. Ide, 7 Orchard Court, Newton, 5074, both of Australia

[21] Appl. No.: 253,192

[22] Filed: Jun. 2, 1994

Related U.S. Application Data

[63] Continuation of Ser. No. 768,917, Jul. 27, 1992, abandoned.

[30] Foreign Application Priority Data

Feb. 5, 1990 [AU] Australia ................................. PJ8440

[51] Int. Cl.⁶ ................................................. A61B 17/60
[52] U.S. Cl. .................................... 606/59; 606/54
[58] Field of Search ................................ 606/57, 58, 59, 606/55, 54, 56, 53, 72, 73, 105

[56] References Cited

U.S. PATENT DOCUMENTS

| | | | |
|---|---|---|---|
| 2,333,033 | 10/1943 | Mraz | 606/57 |
| 3,473,528 | 10/1969 | Mishkin et al. | 606/57 |
| 4,187,841 | 2/1980 | Knutson | 606/57 |
| 4,393,868 | 7/1983 | Teague | 606/59 |
| 4,456,004 | 6/1984 | Kenny | 606/57 |
| 4,475,546 | 10/1984 | Patton | 606/57 |
| 4,488,542 | 12/1984 | Helland | 606/57 |
| 4,662,365 | 5/1987 | Gotzen et al. | 606/59 |
| 4,747,400 | 5/1988 | Koeneman et al. | 606/54 |
| 4,848,368 | 7/1989 | Kronner | 606/57 |
| 4,978,348 | 12/1990 | Ilazarov | 606/57 |
| 4,998,935 | 3/1991 | Pennig | 606/54 |
| 5,021,054 | 6/1991 | Monfardini et al. | 606/57 |
| 5,160,335 | 11/1992 | Wagenknecht | 606/59 |
| 5,207,676 | 5/1993 | Canadell et al. | 606/54 |
| 5,275,599 | 1/1994 | Zbikowski et al. | 606/54 |

FOREIGN PATENT DOCUMENTS

| | | | |
|---|---|---|---|
| 386308 | 9/1990 | European Pat. Off. | 606/57 |
| 3614305 | 11/1987 | Germany | 606/57 |
| 8802462 | 5/1990 | Netherlands | 606/57 |
| 322191 | 11/1971 | U.S.S.R. | 606/57 |
| 727193 | 4/1980 | U.S.S.R. | 606/59 |

*Primary Examiner*—Stephen C. Pellegrino
*Assistant Examiner*—Guy Tucker
*Attorney, Agent, or Firm*—Townsend and Townsend and Crew

[57] ABSTRACT

A unilateral external fixator comprises a telescoping unit which includes telescopically engaging inner and outer parts arranged for limited axial reciprocal movement relative to one another along the longitudinal axis of the unit, the outer part having a central bore extending therethrough, the inner part engaging with sliding fit in the bore and extending the full length thereof, the inner part being non-rotatable about said axis. The bore is made up of hard polymeric material and the inner part is formed of metal. A pair of orthopedic pin clamp assemblies is carried by the inner part adjacent its proximal end and the outer part for selective positioning along the entire length thereof. A lock releasably locks the parts against axial movement.

22 Claims, 6 Drawing Sheets

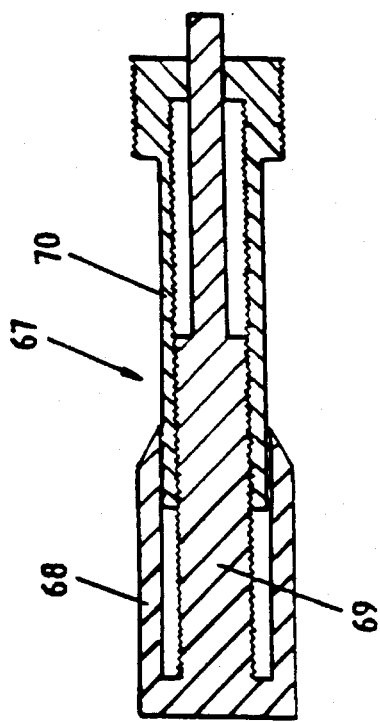
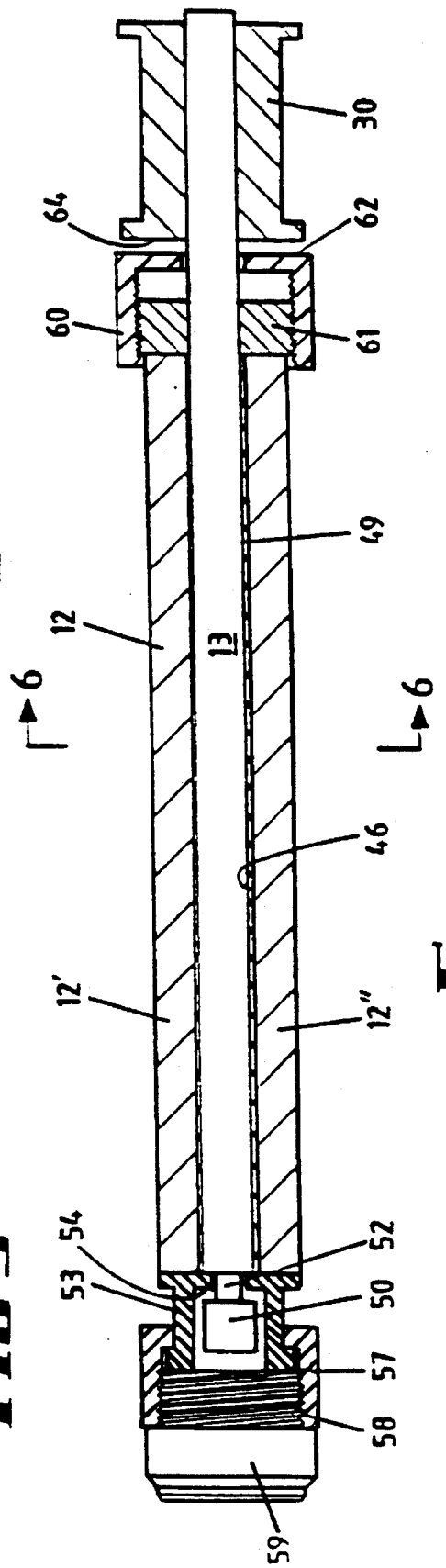
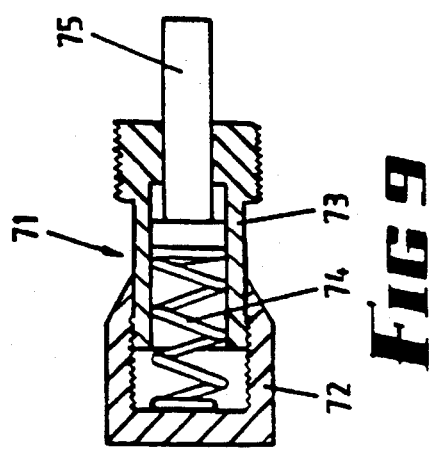
FIG 8
FIG 4
FIG 9

EXTERNAL FIXATION DEVICE

This is a continuation of application Ser. No. 07/768,917, filed Jul. 27, 1992, now abandoned.

BACKGROUND OF THE INVENTION

This invention relates to improvements in and to an external fixation device used in the treatment of bone fractures, and more specifically to an improved unilateral or one-sided, telescopic, single frame fixation device which can provide dynamic axial motion.

The purpose of an external fixator is to hold together by means of pins, the fragments or segments of a fractured bone so that healing may progress while allowing the patients to retain. mobility of neighboring joints. To perform this task, the fixator must be sufficiently rigid or stiff to support the loads imposed on it without allowing excessive movement at the fracture site.

The use of external fixation devices is an established and recommended form of treatment in many forms of limb injury and many different fixation devices have been designed and are known to the applicants. While some of these are generally considered satisfactory, it is believed that most are unnecessarily complex and do not provide the degree of rigidity required for optimal bone healing. In an effort to increase rigidity, designers have resorted to multilateral or multiaxial units (which include more than one external fixation body) but such units are bulky and difficult to handle and are technically complicated. In addition their bulkiness renders access to the wound as well as soft tissue management difficult.

Another drawback associated with known external fixation devices has been their inability to permit the pin clamps-and their attachments to the main body of the fixation unit to be easily and quickly adjusted by the surgeon and the restricted range of movements which such component parts can undergo. This has rendered difficult the entry of the retainer pins and as well the ease with which any rotational misalignment of the fractured bone can be corrected. In addition, there are limitations on the extent to which the spatial orientation of each set of retainer pins relative to the main body of the fixation unit can be varied, such variation being required to enable the unit to be easily installed and to permit the body of the fixator to be positioned parallel to the long axis of the bone, regardless of where the bone fracture occurs whether in a wide or narrow part of the bone.

While certain prior art external fixation devices are designed to provide dynamic axial motion, a problem common to such devices is the high bending moments which occur in the retainer pins and therefore the main body of the fixation unit, during ambulation. Studies have shown that these high bending moments cause the telescoping parts of the unit to jam especially where sliding friction is relied upon and the telescoping parts are made of the same metal, or metals having a high coefficient of friction. These units may provide a consistent dynamic axial motion (i.e. axial telescoping motion) at the fracture site by the application of a load through the fixator pins by an externally applied motor (referred to as "active dynamization"), but they cannot generally be relied upon to provide consistent and reliable passive dynamization through ambulation.

It is important that the fixator be sufficiently stable so that dynamic axial motion is ensured through telescoping of the device and not by instability of the fixator. Repeated axial movements may cause the telescoping unit to loosen or jam with time, which in turn may alter drastically the rigidity of the fixator and the efficacy of dynamization. For example, a significant problem with certain prior art units is their rotatory instability. One solution to this problem was to use a key-lock system, i.e. where the inner and outer telescoping members are part circular and a key engages within a groove extending along the inner member. Enhanced rotatory stability can be provided by a tighter fitting key-lock, but this results in stiction of the contact areas of the key-lock. Loose-fitting key-locks, where a keying pin engages in a key-way formed in the inner member, prevent this complication but cannot provide adequate rotatory stability.

Fixators have also been developed relying on rolling friction between the telescoping parts rather than sliding friction, these utilizing roller bearings rolling in ball bearing races. However, due to the fact that micromotion required for external fixators is in the order of 1 mm or less, such ball or roller bearings providing this motion will not roll but rather rock and will therefore brinell. Such brinelling is a cause of instability and/or jamming, which should be avoided in dynamizing external fixators.

A still further deficiency of some known unilateral, telescopic external fixators is their inability to vary or alter the rigidity of the device to axial motion of the telescoping parts during the course of fracture healing. It has been found that greater rigidity is required in the early phases of fracture healing and less rigidity later. It is desirable that means be provided so as to prevent passive motion during early stages of fracture healing of the telescoping parts of the fixator device until a set or predetermined load is exceeded.

SUMMARY OF THE INVENTION

One object of the present invention therefore is to provide an improved unilateral, telescopic external fixation device which is of simple design, easy to handle and is more versatile in its ability to vary the orientation and positioning of the pin clamps and in turn the orientation and positioning of the retainer pins fixed in the clamps.

It is another object of the present invention to provide an improved unilateral, telescopic external fixation device which can consistently, reliably and efficiently provide dynamization (both active and passive) without jamming of the telescoping parts.

It is yet another object of the present invention to provide an improved unilateral, telescopic external fixation device which can have its resistance to axial motion readily altered during the course of fracture healing.

It is yet a further object of the present invention to provide an improved unilateral, telescopic external fixation device-which can provide an extremely stable, rigid structure thereby promoting more rapid healing and early ambulation.

According to one aspect of this invention therefore, an improved unilateral, telescopic external orthopedic fixation device comprises an elongate telescoping unit comprised of a pair of telescopically engaging inner and outer parts adapted for relative axial reciprocal movement along an axis which coincides with the central longitudinal axis of said unit, and releasable locking means for releasably locking said parts against relative axial movement, a pair of pin clamps respectively carried on the telescoping parts for clamping one or more orthopedic retainer pins spaced lengthwise of the clamp and extending transversely thereof, clamp connection means on each of the telescoping parts of said elongate telescoping unit for connecting a respective said clamp thereto, each said clamp connection means comprising a clamp holder having a first axis of rotation spaced radially from said longitudinal axis of the telescoping unit whereby said clamp holder when in an unlocked condition, along with its associated said clamp can bodily rotate about said first axis, said clamp holder being adjustably supported for slidable movement lengthwise along its said first axis whereby the spatial position of its associated said clamp can be varied by varying the radial distance (measured along said first axis) between said clamp and the telescoping unit, and wherein each said clamp is rotatably supported by said clamp holder so as to permit the clamp to bodily rotate about a second axis of rotation extending lengthwise thereof and at right angles said first axis.

With the above arrangement, the pin clamps of the fixator together with the set of pins can rotate from a transverse through to a vertical plane. This allows the pins to be placed horizontally at the end of the bone, which is desirable for metaphysical fractures of long bones.

The arrangement also permits the pin clamps to be tilted through a wide arc, which is required for spiral and vertical fractures which may have a wide angular range of the plane of the fracture.

The ability of the clamps to slide horizontally allows rotation of the bone fragments without loss of axial alignment of the fixator and also a wide variation of the angle of insertion of the pins into the bone. Malalignment of the longitudinal axis of the fixator from that of the tibia lessens the potential for dynamic axial motion of the device. Known dynamizing fixators allow rotation of the bone fragments only by axial deviation of the body of the fixator from the longitudinal axis of the tibia.

Preferably each said clamp connection means (or at least that on the outer telescoping part) further comprises bracket or connector means slidably supported on its associated said telescoping part whereby the entire clamp connection means, when in an unlocked condition, along with its associated said clamp can slide longitudinally of said telescoping unit. The positioning of at least one of the pin clamps at any location along the full length of the outer telescoping part ensures minimal separation of the inner pins. Preferably, one of the bracket means is fast with the free end of the inner telescoping part, while the other bracket means can slidably locate along the length of the outer telescoping part. In this way the separation of the pin clamps and the pins does not necessitate any adjustment to the telescoping parts, which contrasts with prior art units which require relative axial separation thereof. This also allows the telescoping parts be in contact with one another over a major portion of the length of the fixator, which gives rise to decreased bending movements and lessens the likelihood of the "jamming" of the unit during dynamic axial motion.

In another preferred form of this invention, said bracket means is rotatably supported on its said telescoping part whereby said clamp connection means can be rotationally adjusted about an axis which coincides with or is parallel with the longitudinal axis of said telescoping unit, to assume different angular positions relative to the telescoping unit.

In another preferred form of this invention, each said clamp connection means comprises a swivel block interconnected between the bracket means and the clamp holder and being rotatable, when in an unlocked condition, about a third axis which extends at right angles to both the axis of the telescoping unit and said first axis. This permits the block, along with its clamp holder, to swivel about said third axis and be set in a number of different angular positions relative to the telescoping unit.

Preferably the connector or bracket means comprises an attachment body which encircles the associated telescoping part and is provided with a locking member, e.g. a clamping screw or bolt, which when tightened causes said body to clampingly engage against said telescoping part and locking the connector means against both rotational and longitudinal movement relative to the telescoping unit. Preferably the body comprises a pair of hinged halves which are hingedly joined together along an axis parallel to the axis of the fixator, with the clamping or locking screw clamping together the free ends thereof on the opposite side of the fixator body. This allows a clamp to be easily removed from or added to the fixator even when the fixator remains attached to a patient.

Preferably, the pin clamps have a 360° horizontal angular range which permits the body of the fixator to be swung around from one side of the leg to the other, thereby providing complete access to the wounds during operative soft tissue closure or wound care.

In yet another preferred embodiment, each said clamp holder comprises a transversely extending short length pin or shaft journalled for rotation about said first axis and fixedly carrying at its distal end a pair of semi-circular fingers or jaw members, the inner peripheral walls of which together define a through opening in which is rotatably received a respective said clamp to enable said clamp to be rotated through 360°, this in turn permitting the orientation of the fixator pins held therein to be similarly varied.

According to another aspect of the present invention, there is provided an improved unilateral telescopic external fixation device comprising a main telescoping unit comprised of a pair of elongate telescopically engaging pans adapted for relative axial sliding movement along the longitudinal axis of said telescoping unit, the outer one of said parts constituting a housing having a bore extending therethrough, the inner one of said parts constituting a rod engaging with a sliding fit in the bore and being non-rotatable about said axis, the profile of said rod and said bore each being non-circular and having at least one flat side, and wherein said rod is formed of metal, preferably stainless steel, and the surface of said bore comprises hard polymeric material, whereby sliding friction between the parts, during said relative axial sliding movement, is minimized.

Preferably, the housing has a cylindrical outer wall surface and is comprised of two identical axial halves secured together by clamping screws. The housing may however be formed as a unitary member.

By using dissimilar materials for the inner rod and the bore surface of the cylindrical housing within which the piston moves, the sliding friction is very much reduced (in comparison to using similar metals, for example) and there is less likelihood of the unit jamming during dynamization thereof. Experiments conducted by the inventors have shown that the combination of a suitable polymeric material and stainless steel affords a most significant improvement, in terms of frictional resistance, in comparison to pairs of similar metals or even dissimilar metals, e.g. stainless steel/ hard chrome stainless steel, stainless steel/brass.

Preferably the bore of the cylindrical housing is lined with a layer of hard polymeric material, preferably acetal, and in particular material sold under the proprietary name "ERTACETAL" (polyoxymethylene). The lining may be provided by means of elongate flat strips inserted in the bore and coextensive therewith, each strip bearing against a respective planar bore surface extending along the length of the bore. Any hard polymeric material having high abrasion and wear resistance and a low coefficient of friction would be suitable. In addition to acetals, other examples may include high density polyethylene and polypropylene.

In a preferred arrangement, said bore is rectangular, and said rod has a rectangular cross-sectional shape. The shape may also be triangular.

In another preferred arrangement, said rod comprises flat upper and lower surfaces which are joined along their longitudinal margins by curved sidewall surfaces, and said insert comprises a pair of diametrically opposed approximately D-shaped insert members fixedly secured to the cylindrical bore with the planar faces of said insert members engaging against respective flat surfaces of the rod, said insert members being formed of hard polymeric material.

Preferably, said rod extends through the entire length of the housing and is provided at its distal end with a limit wall which cooperates with a radial abutment surface at the distal end of the housing to permit limited relative axial movement only between the rod and the housing, such movement preferably being in the order of 5 mm. In this manner, the rod maintains contact with the bore over a major portion of the length of the rod, which promotes stiffness and rigidity, and minimizes the effect of possible bending moments, which in turn facilitates dynamization.

In yet another aspect of the present invention, an improved unilateral, external fixation device comprises a pneumatically operated or electric motor at the distal end of said cylindrical housing and being coaxially aligned therewith, said motor being adapted to provide dynamic axial motion or dynamic axial loading of the bone fragments of the fractured bone.

Preferably the motor is arranged to provide micromotion at a frequency of approximately 0.5 Hz and at an adjustable excursion of 0.1 mm to 1.0 mm.

In a further aspect of this invention, the telescoping unit is provided at its distal end with removable calibrated axial distraction means comprising a longitudinally extending threaded rod arranged coaxially within the unit for effecting axial separation of the telescoping parts and in turn distraction of the bone parts, so as to allow bone lengthening procedures.

In yet another aspect arrangement, the telescoping parts of the telescoping unit cooperate with an adjustable spring mechanism removably housed at the distal end of the outer part of the unit and arranged to provide an adjustable axial loading force to resist motion of the telescoping parts and to prevent relative axial movement of the telescoping parts until a set (predetermined) load is exceeded. The adjustable spring will not allow dynamic axial motion to occur before said set load is applied. This load will be set high during the early phase of fracture healing and set low during the latter phase of fracture healing.

In order to more fully explain the applicants' invention, several embodiments are described hereunder in some further detail but with reference to and illustrated in the accompanying drawings in which,

BRIEF DESCRIPTION OF THE DRAWINGS

FIG. 4 is a longitudinal sectional view of the telescoping unit shown in FIG. 1 (omitting the clamp assemblies for the sake of clarity);

FIG. 8 is a longitudinal sectional view of an axial distraction unit for use with the fixator shown in FIG. 1;

FIG. 9 is a longitudinal sectional view of an axial loading unit for use with the fixator shown in FIG. 1.

DESCRIPTION OF THE PREFERRED EMBODIMENTS

Figure 1:
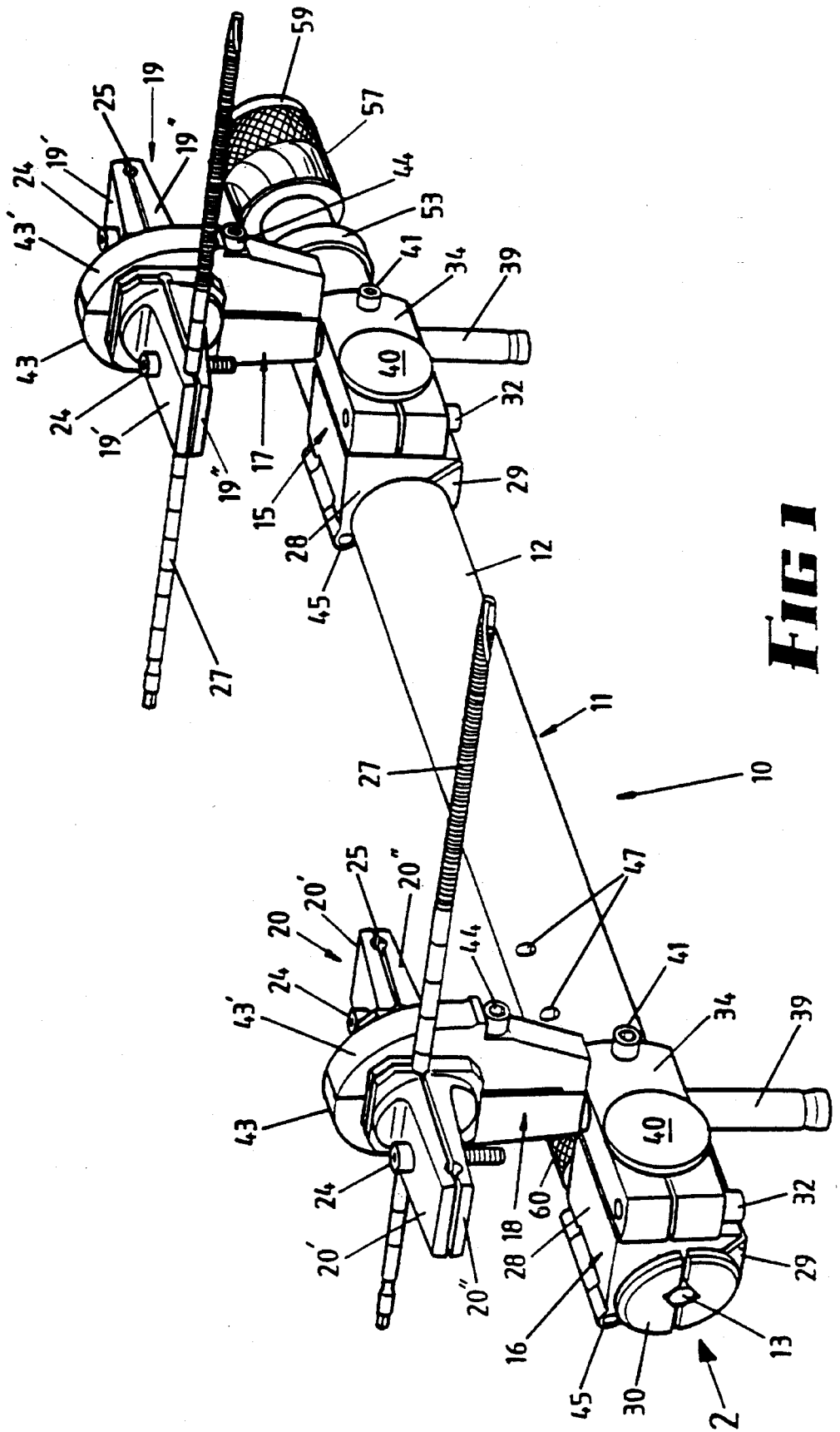
FIG. 1 is a perspective view of an external fixator according to a first embodiment of the invention.
Figure 2:
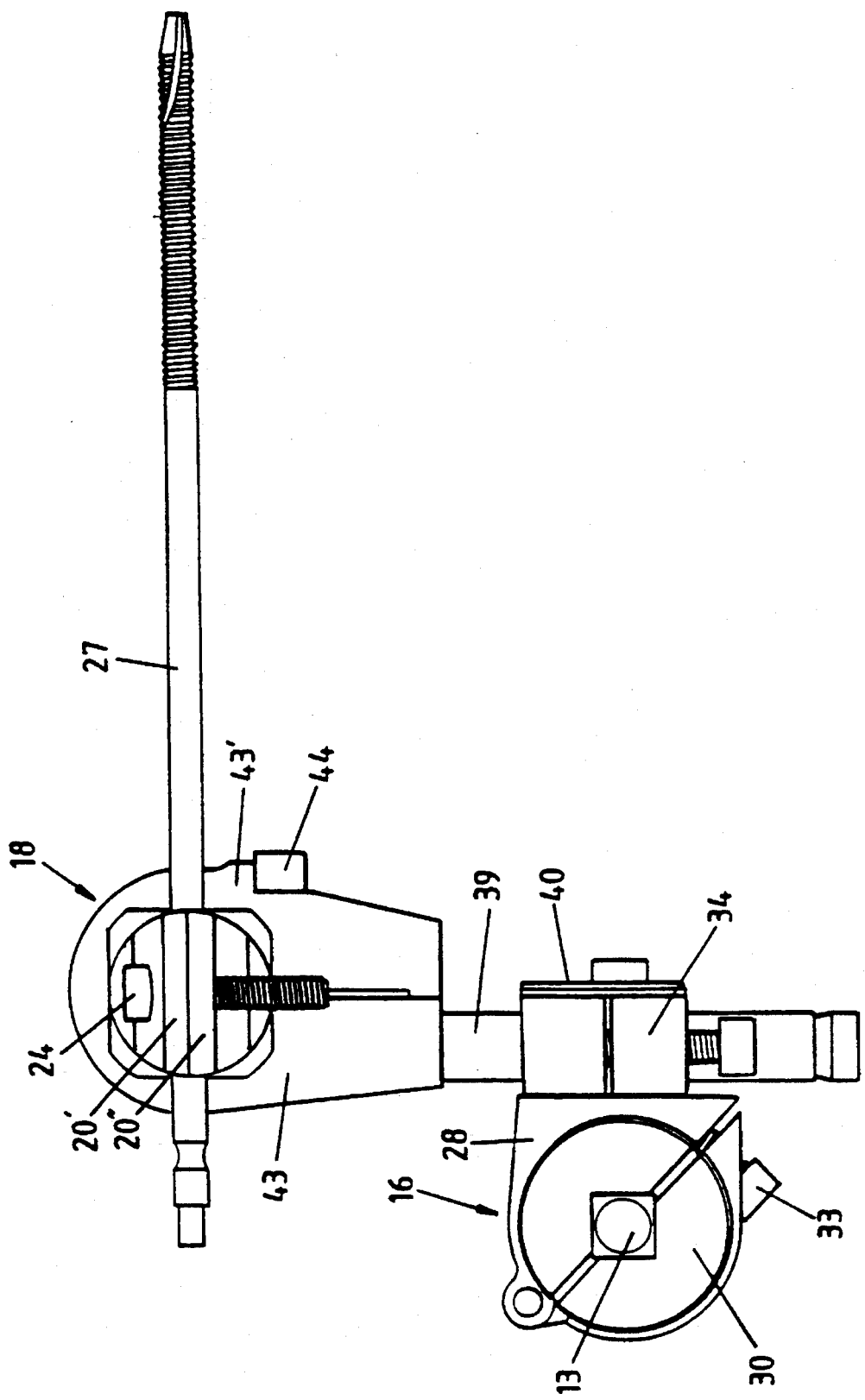
FIG. 2 is an end elevational view of the fixator looking in the direction of arrow 2 of FIG. 1.

In the embodiment illustrated in FIGS. 1 to 4, an orthopedic external fixation device 10 comprises a main telescoping unit 11 which itself includes an outer cylindrical housing 12 in which is reciprocally housed a telescoping rod 13, clamp connectors 15, 16 on the cylindrical housing 12 and the head end of the rod 13 respectively, clamp holders 17, 18 associated with each said clamp connector 15, 16 and pin retainer clamps 19, 20 rotatably supported by the clamp holders 17, 18, respectively. Each of the clamps 19, 20 comprises pairs of opposed grooved clamp plates 19', 19" and 20', 20", which are clamped together by means of clamping screws 24 so as to form transversely extending through opening 25 for receiving fixator retainer pins 27 arranged to be spaced lengthwise of the clamps 19, 20 and projecting transversely thereof. The pins 27 are of known construction.

In this embodiment, the clamp connectors 15, 16 each comprises a pair of hinged connector portions 28, 29, arranged to encircle the cylindrical housing 12 and the circular enlarged head 30 (formed by two halves) at the free end of the rod 13, respectively, the connector portions 28, 29, when in their loosened condition, permitting the clamp connectors 15, 16 to be rotated about an axis which coincides with the central longitudinal axis of the telescoping unit 11 and, in the case of connector 15 also slidably displaced longitudinally along the length of the housing 12. With the clamping screws 33 to FIGS. 2 and 3) in their tightened condition, the inner bore surfaces of the connector portions 28, 29 clampingly engage against the outer cylindrical surface of the cylindrical housing 12 and the piston head 30 respectively so as to immobilize the brackets 15, 16.

Figure 3:
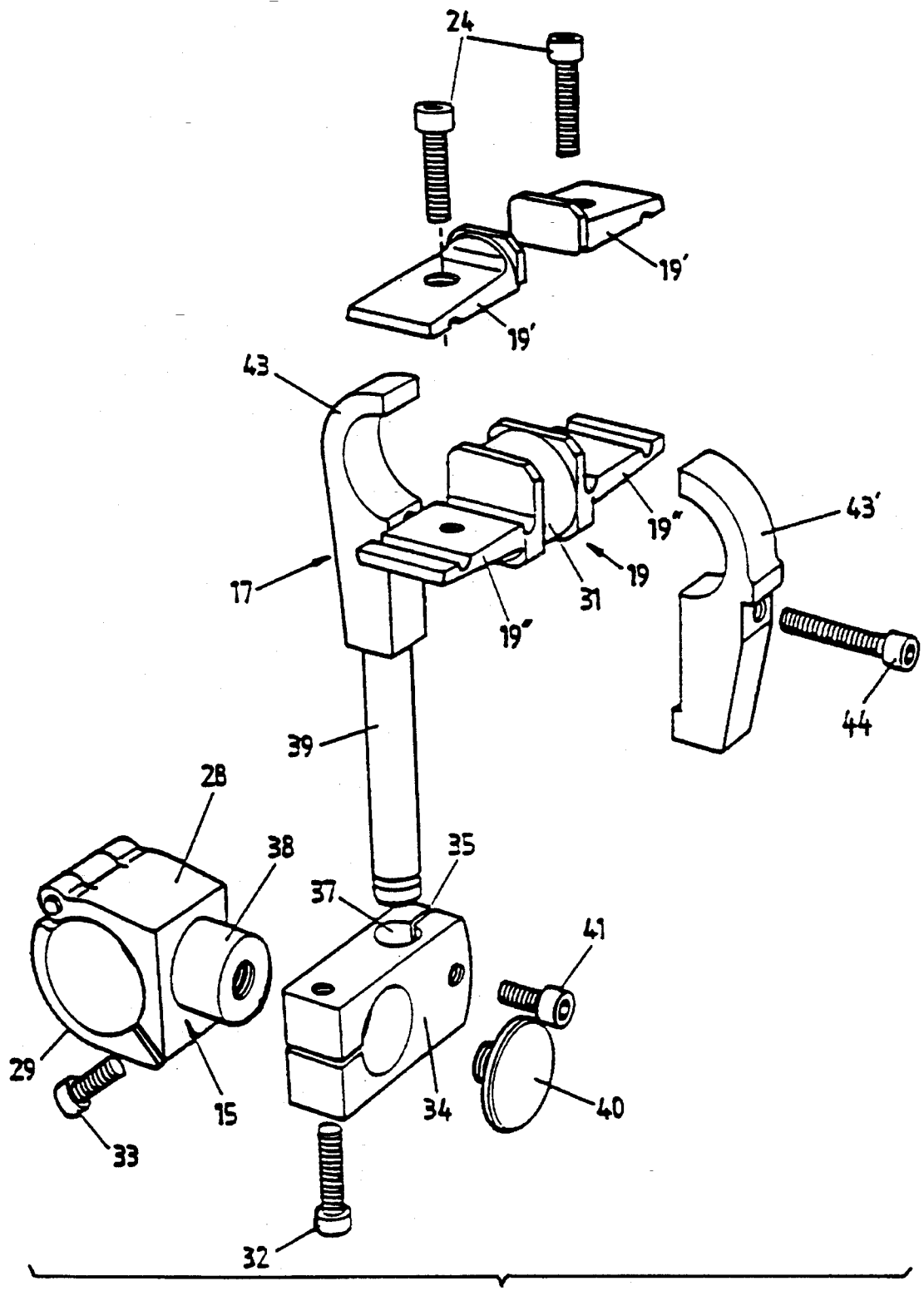
FIG. 3 is a exploded perspective view of one of the clamp assemblies shown in FIG. 1.

As shown in FIG. 3, each clamp 19, 20 is a three-piece assembly comprising two identical plates 19' and a unitary member 31 containing the plates 19". The pieces may be die cast of aluminum or aluminum alloy. With this arrangement, the pins 27 can be removed without removing the clamp from its holder.

Supported on portion 28 of the connectors 15, 16 are swivel blocks 34, radially spaced from the cylindrical housing 12 of the telescoping unit 11, each block 34 being formed with a transverse horizontal slot 35 extending inwardly from one end of the block and communicating with a transversely extending circular through-opening 37 in which is rotatably received a solid cylindrical pin or shaft 39 which forms a short length stem that is part of the clamp holder 17, 18.

Each block 34 is rotatably mounted on a stub shaft 38 projecting radially from a side of portion 28, and releasably locked therewith by means of clamping screws 32, whereby, with the screws 32 loosened, the blocks 34, along with the holders 17, 18, can swivel about an axis which intersects the central axis of the unit 10 at right angles and is also at right angles to the axis of the shaft 39.

The rotation of the holders 17, 18 along with their pin clamps 19, 20 and pins 27 about the axis of the shaft 39 permits the pins to be inserted longitudinally or transversely, which is desirable in situations involving bones of varying diameter.

A cover member 40 having a threaded stem which threadably engages in a threaded central bore formed in the shaft 38 prevents dislodgement of the block 34.

Clamping screw 41, when tightened, frictionally clamps the shaft 39 against both rotational and slidable movement relative to the block 34. It will of course be appreciated that when the screw 41 is in its untightened condition, the clamp holders 17, 18 can be rotated about the axis of the shaft 39 and locked in any desired orientation and also slidably adjusted lengthwise of the axis of the shaft 39.

Each clamp holder 17, 18 also includes a pair of semi-circular lugs 43, 43' which cooperate together to form a circular opening for clampingly receiving the clamps 19, 20. An adjustment screw 44 is used to fasten the lugs 43, 43' together, and which, when untightened, allows the clamp 19, 20 to be bodily rotated (along with its pins 27) to any desired angular setting.

Figure 10:
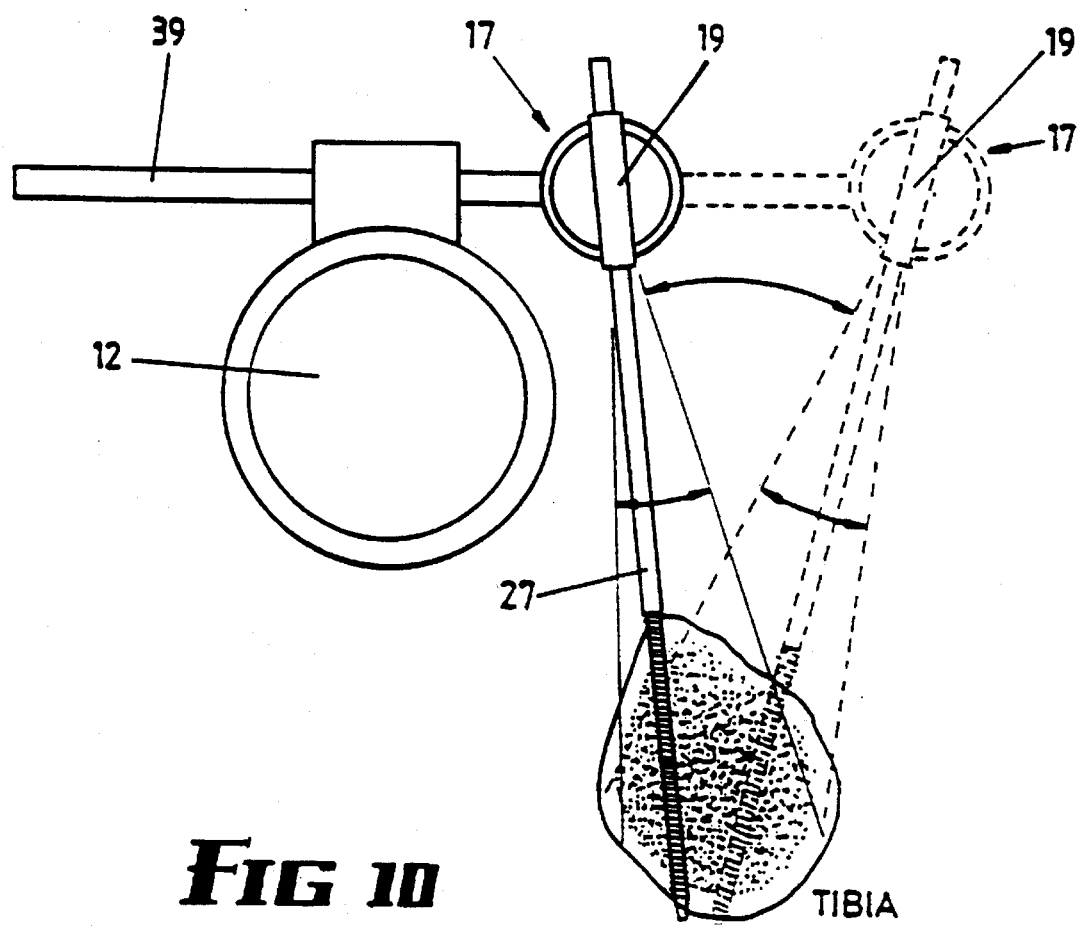
FIG. 10 is a schematic elevational view of the fixator of this invention which shows some of the adjustments which can be achieved with the clamp assembly shown in FIG. 1.

The ability of the clamp holder 17, 18 to both rotate about the axis of shaft 39 and to slide longitudinally along that axis has been shown to greatly facilitate the placement of the retainer pins into the bone fragments and also the correction of any rotational misalignment of the bone fragments without altering the longitudinal alignment of the housing 12 to the axis of the bone, e.g. tibia, while the ability of the clamps 19, 20 to bodily rotate about an axis at right angles to the axis of the shaft 39 lends the unit suitable for approaching the bone through a wide angular range. These features can be clearly seen from FIG. 10 of the drawings, which shows how the pin clamp 19 can be horizontally displaced from the housing 12, and its orientation altered, which ensures a wide range of available pin angles.

The ability of the clamp connectors 15, 16 to slide along the cylindrical housing 12 facilitates optimal positioning of the retainer pins 27 relative to the fracture site. It is an advantage of the present invention that more than one clamp connector can be supported on the cylindrical housing 12, and by virtue of the versatility of the range of movements which the clamp connector, holder and clamp can undergo, one is able,to position pins on opposite sides of the housing 12 of the unit 11, so as to allow "triangulation" and provide enhanced rigidity.

The hinge 45 which pivotally joins the portions 28, 29 of the connectors 15, 16 permits the connectors to be readily removed from the housing 12 even with the unit 11 attached to a bone.

Figure 5:
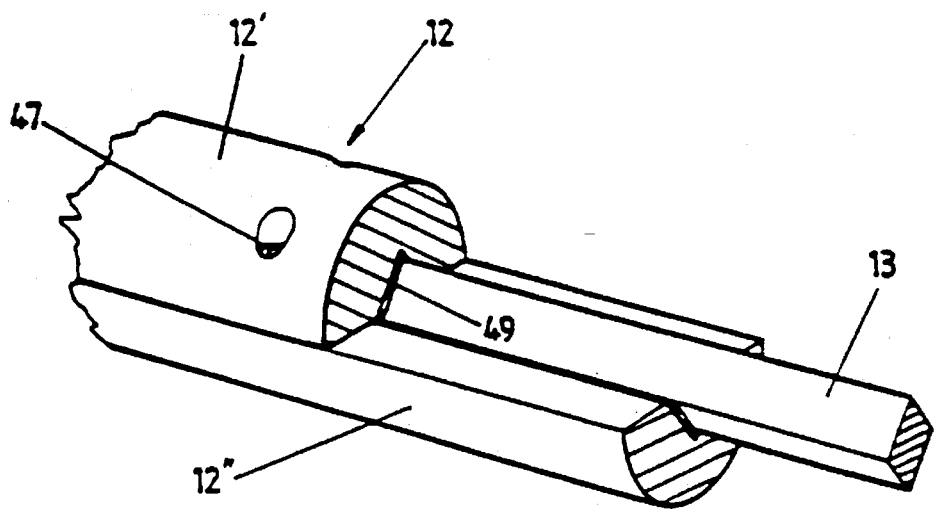
FIG. 5 is a fragmentary perspective view, partly in section of the telescoping unit of FIG. 4.
Figure 6:
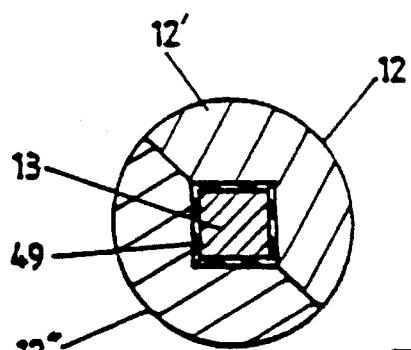
FIG. 6 is a radial cross-sectional view along the lines 6—6 of FIG. 4.

Referring to FIGS. 4 to 6 of the drawings, the rod 13 of the telescoping unit 11 is formed of stainless steel having highly polished outer surface and is of square cross-section. The rod 13 slidably engages with a sliding fit in a bore 46 which extends through the full length of the housing 12, the bore 46 also being of square cross section. The housing 12 is preferably formed of aluminum and comprises two diametral halves 12', 12" secured together by screws 47. The bore 46 is lined by means of replaceable strips 49 of hard polymeric material, e.g. ertacetal, which is abrasion resistant, has a low co-efficient of friction and good surface lubricity, such an arrangement minimizing the sliding friction between the rod 13 and the bore surface 46, as a result of which the moving parts of the unit 11 are less likely to jam when subjected to bending moments, in comparison with existing art. Of course, the liner 49 may be in the form of angle inserts snugly fitted into the bore 46 of the housing 12. The four strips 49 are held loosely in the bore 46 against respective planar surfaces formed therein and can be easily replaced if and when necessary.

The outer end of the rod 13 terminates in an enlarged head 30 fast therewith, and around which is clamped connector while the inner or distal end of the rod 13 threadably connects to a limit block 50 via a threaded stem 52, coaxial therewith. The block 50 is housed in an extension piece 53 of the housing 12 and fixed thereto and is designed to limit axial movement of the rod 13 through a preset range, depending on the healing requirements of the fracture, the block 50 cooperating with a radial abutment flange 54 to constrain rod movement in the extension direction. Movement in the retraction direction of the rod is constrained by the end wall of the rod 13 abutting against the other side of the flange 54 or by the head abutting against a locking collar 60 on the proximal end of housing 12.

The extension piece 53 supports a slidable joining collar 57 which has an internal thread 58 for receiving a threaded end plug 59.

The proximal end of the housing 12 is provided With a locking collar 60 which has an internal thread which threadingly engages an external thread on end block 61 secured to the end of the housing 12, the block 61 having a central opening through which passes the rod 13. The arrangement is such that as the locking collar 60 is rotated to its locked position, the end wall 62 of the collar 60 bears against the facing wall 64 on the head 30 of the rod 13 and, upon further tightening, the rod 13 is axially displaced in the extension direction until the limit block 50 abuts against the flange 54, whereupon the rod 13 is locked against any movement, the housing 12 and rob 13 thereby being fixedly secured with respect to one another. The locked condition is required when any shortening or collapse of the rod 13 is to be prevented. It should be realized that the threaded collar 60 can also be used to provide adjustment of the limit of movement of the rod 13 in its retraction direction. This limit can be preset by the surgeon.

With the locking nut 60 in its loosened or unlocked condition, the unit can be subjected to dynamic axial loading which can either be "passive", achieved through the action of ambulation, or "active", effected through a motor unit (not shown) attached via the collar 57 at the distal end of the cylindrical housing 12 and coaxially aligned therewith. Preferably the motor is pneumatically or electrically operated.

Figure 7:
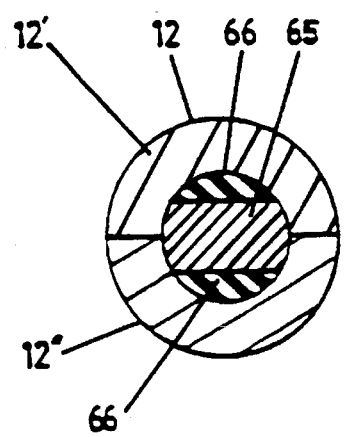
FIG. 7 is a sectional view similar to FIG. 6 of a telescoping unit according to a second embodiment of the invention.

In an alternative embodiment shown in FIG. 7 the rod 65 is formed with two flat sides joined by two curved side walls, while the bore of the housing 12 is circular and has fitted therein a pair of inserts 66 formed of hard polymerical material. The inserts 66 are D-shaped and are restrained against rotation by means of grub screws (not shown) extending through the wall of the housing 12. Once again, the presence of the polymeric inserts 66 significantly reduces the effect of sliding friction.

In the above-described embodiments, each of the clamping screws comprises a hexagonal recess or depression in the head thereof, and rotational adjustment of such screws is effected by means of a known hexagonal key spanner.

Referring to FIG. 8 of the drawings, a calibrated lead screw device 67 is shown and which can be attached to the unit 11 (by removing end plug 59) via the collar 57, the device 67 cooperating with the rod 13 to effect controlled relative axial movement between the rod 13 and the cylinder 12, which in turn effects distraction of the bone fragments, this being necessary to allow the bone lengthening procedures. The device 67 comprises an adjustment member 68 having a threaded stem 69 which is screwed into a threaded bore of body portion 70 which in turn is screw connected to the collar 57. The stem 69 projects through the body portion 70 and bears against an intermediate insert located between the rod 13 (the block 50 having been removed).

Referring to FIG. 9 of the drawings, there is shown an axial loading device 71 attachable to the collar 57 of the unit 11 to lie coaxial therewith, the device 71 being provided with an adjustable nut 72 which is screwed to a tubular body 73, and a resilient compression spring 74 housed within the nut and the body 73, the spring 74 in turn making pressure contact against a pin 75 which projects axially from the end of the body 73 and bears against the end of the rod 13, when the device 71 is so attached. The device 71 thus coacts with the rod 13 to provide an adjustable spring resistance to movement of the rod 13 in such a manner that any movement of the rod 13 is inhibited until such time as a set or predetermined load is exceeded. As explained hereinbefore, greater rigidity is required in the early phases of fracture healing and less rigidity later on. The adjustable spring mechanism is designed so as not to allow dynamic axial motion to occur before the set load is applied. The required load will be set high during the early phase of fracture healing and in turn set low during the late phase of fracture healing.

It will be realized that the material selection for the telescoping parts 12, 13 can be different from that stated above. For example, the rod 13 may be formed of titanium or anodized aluminum, while the housing 12 may be of a suitable hard plastics material. The rod 13 may even be lined or coated with a suitable wear resistant plastics material having good surface lubricity and a low coefficient of friction, e.g. teflon. Still further, it may be possible to coat the bore surface of the housing 12 with a layer of hard polymeric material.

A brief consideration of the above-described embodiments will indicate that the invention provides an improved unilateral external fixation device which is extremely versatile, completely adjustable, easy to use and provides consistent reliable and effective dynamic axial motion.

What is claimed is:

1. A dynamizing telescopic external fixator for providing controlled motion to a bone fracture site, comprising:

a main telescoping unit having a central longitudinal axis and comprising elongate telescopically engaging inner and outer parts configured for limited relative oscillatory movement along the longitudinal axis of the unit, the outer one of said parts constituting a housing having a cylindrical outer surface extending along its entire length and a central bore extending therethrough, said bore having a non-circular profile, the inner one of said parts constituting a rod which engages with a sliding fit in the bore and being of a length so that it extends approximately the full length thereof with one end of said rod projecting outwardly from a first end of said housing, said rod having a non-circular profile which has at least one planar surface and being non-rotatable about said axis;

first and second orthopedic pin clamp assemblies;

first and second support means respectively supporting said first and second pin clamp assemblies on said telescoping unit in spaced relation therewith, said first support means for said first pin clamp assembly being fitted to the rod adjacent said one end thereof, said second support means for said second pin clamp assembly being coaxially supported on the cylindrical surface of the housing and being adjustably positionable rotatably on the housing about its said axis and also slidably along the length thereof;

each said pin clamp assembly comprising a pin clamp holder and pin clamp for removably securing at least one fixator pin therein, said fixator pin of the first pin clamp assembly being positionable on one side of a bone fracture site, said fixator pin of the second pin clamp assembly being positionable on another side of a bone fracture site;

an incrementally adjustable stop member threadably attached coaxially to said first end of said housing and cooperating with said first support means for providing selective adjustment of the relative oscillatory movement of said rod relative to said housing which includes a retraction and an extension stroke, said stop member being adjustable between a locking position which prevents any retraction movement of the rod and a release position which allows the rod to oscillate relative to the housing through a predetermined axial distance to impart a predetermined axial micromotion to the bone fracture site; and limit means coupled to said rod for limiting the movement of the rod in the direction of its extension stroke.

2. A dynamizing telescopic external fixator according to claim 1 wherein said stop member comprises a locking collar having an internal thread which threadably engages an external thread on the outer surface of said housing adjacent said first end.

3. A dynamizing telescopic external fixator according to claim 1 wherein said limit means comprises a limit block which cooperates with an abutment on the housing at a second opposite end of said housing.

4. A dynamizing telescopic external fixator according to claim 1 wherein said limit means comprises an axial loading device which includes an adjustable spring mechanism attached coaxially to said second end of said housing and cooperable with said rod to provide an adjustable axial loading force to resist motion of said rod and to prevent said limited relative oscillatory movement of the telescoping parts until a predetermined load is exceeded.

5. A dynamizing telescopic external fixator according to claim 1 wherein said rod and said bore have a profile which is rectangular or square.

6. A dynamizing telescopic external fixator according to claim 5 wherein each of the planar surfaces of the bore is lined with a layer of hard polymeric material.

7. A dynamizing telescopic external fixator according to claim 1 wherein said rod is formed of metal, and the surface of said bore comprises hard polymeric material.

8. A dynamizing telescopic external fixator according to claim 7 wherein said metal is stainless steel and said polymeric material is acetal.

9. A dynamizing telescopic external fixator according to claim 1 wherein said housing comprises two identical axial halves secured together by fastener means.

10. A dynamizing telescopic external fixator according to claim 1 wherein each of said support means comprises a sleeve-like mounting bracket slidably supported on its associated said telescoping part, releasable locking means for clampingly engaging said mounting bracket to its associated said telescoping part, arranged so that when the locking means is released, the bracket and its associated pin clamp assembly can slide longitudinally of said telescoping unit.

11. A dynamizing telescopic external fixator according to claim 10 wherein the mounting bracket of said second pin clamp assembly has a cylindrical inner bore surface which surrounds the cylindrical surface of the housing, such that the bracket and its associated pin clamp assembly can be rotationally adjusted about an axis which coincides with the longitudinal axis of said telescoping unit for assuming different angular positions relative to the telescoping unit.

12. A dynamizing telescopic external fixator according to claim 11 wherein each said mounting bracket comprises a pair of bracket halves which surround their associated telescoping part, said releasable locking means being arranged to clampingly engage said halves against the periphery of said part to thereby hold same against both rotational and sliding movement relative to the telescoping unit.

13. A dynamizing telescopic external fixator according to claim 12 wherein said halves are hingedly joined together along a hinge axis parallel to the axis of said telescoping unit, and said locking means comprises a clamping screw clamping together the adjacent ends of said halves on the side opposite to said hinge axis.

14. A dynamizing telescopic external fixator according to claim 1 wherein each said clamp holder comprises a short length stem adjustably rotatably and slidably mounted in its associated said support means, said stem defining a first axis of rotation which is spaced from and extending approximately transversely of said telescoping unit, whereby said clamp holder and its associated said pin clamp can bodily rotate about and slide lengthwise along said first axis to thereby permit the spatial position of its associated said pin clamp to be varied relative to the telescopic unit;

means for locking each said clamp holder against said bodily and said slidable movement; and wherein each said pin clamp is rotatably supported by said clamp holder so as to permit the pin clamp to bodily rotate about a second axis of rotation extending lengthwise thereof and at right angles to said first axis.

15. In an improved telescopic external fixator including:

a main telescopic unit having a central longitudinal axis and which itself comprises elongate inner and outer parts adapted for relative axial movement along said axis, first and second orthopedic pin clamp assemblies each comprising a pin clamp holder and a pin clamp for removably securing at least one fixator pin therein, and support means respectively supporting said first and second pin clamp assemblies on said inner and outer parts of the telescoping unit in spaced relation therewith;

the improvement comprising that each said clamp holder has a short length stem adjustably rotatably and slidably mounted in its associated said support means, said stem defining a first axis of rotation which is spaced from and extending approximately transversely of said telescoping unit, whereby said clamp holder along with its associated said pin clamp can bodily rotate about and slide lengthwise along said first axis to thereby permit the spatial position of its associated said pin clamp to be varied without adjusting the telescopic unit;

means for locking each said clamp holder against said bodily rotation and said slidable movement; and wherein each said pin clamp is rotatably supported by said clamp holder so as to permit the pin clamp to bodily rotate about a second axis of rotation extending lengthwise thereof and at right angles to said first axis.

16. An improved telescopic external fixator according to claim 15 wherein said clamp holder support means coupled to said outer part is adjustably positionable rotatably thereon whereby its associated said clamp holder together with the pin clamp can be rotationally adjusted about an axis which coincides with the central longitudinal axis of said telescoping unit for assuming different angular positions relative to the telescoping unit.

17. An improved telescopic external fixator according to claim 15 wherein each said clamp holder support means includes a swivel block which is adjustably rotatable about a third axis which extends at a right angle to both said axis of the telescoping unit and said first axis, the stem of each said clamp holder being journalled for rotation in a bore formed in a respective said swivel block.

18. An improved telescopic external fixator according to claim 17 wherein one of said clamp holder support means is fastened to a free end of the inner telescoping part, the other clamp holder support means being slidably adjustably positioned along the length of said outer telescoping part.

19. An improved telescopic external fixator according to claim 18 wherein each said clamp holder support means comprises a mounting bracket which itself comprises a pair of bracket halves which surround their associated telescoping part, and locking means for clampingly engaging said bracket halves against the periphery of said part to thereby lock same against both rotational and sliding movement relative to the telescoping part.

20. An improved telescopic external fixator according to claim 19 wherein said bracket halves are hingedly joined together along a hinge axis parallel to the axis of said telescoping unit, and wherein said locking means comprises a clamping screw clamping together adjacent opposing ends of said halves on the side opposite to said hinge axis.

21. An improved telescopic external fixator according to claim 15 wherein each said clamp holder comprises a pair of arcuate fingers or jaws carried at the distal end of said short length pin or shaft, said fingers or jaws having inner peripheral walls which together define a through opening in which is rotatably received a respective said pin clamp to enable said clamp to be rotated through 360°, and in turn permit the orientation of the fixator pins held therein to be similarly varied.

22. An improved telescopic external fixator according to claim 21 wherein each said pin clamp is a three-piece assembly comprising a pair of separate identical axially aligned spaced-apart half plates each having a plurality of grooves spaced lengthwise thereof and extending across an inner face thereof, a unitary member comprising a central circular bearing portion which makes bearing contact with said inner peripheral walls of said fingers and a pair of plate portions projecting from opposite sides of said bearing portion and which cooperate with said half plates to form transversely extending through openings for clampingly receiving said fixator retainer pins, and clamping screws for clamping together said plates to respective said half plates.

* * * * *